US005891462A

United States Patent [19]
Carrara

[11] Patent Number: 5,891,462
[45] Date of Patent: Apr. 6, 1999

[54] COMPOSITION FOR TRANSDERMAL ADMINISTRATION OF AN ESTROGEN

[75] Inventor: Dario Carrara, Buenos Aires, Argentina

[73] Assignee: Permatec N.V., Curacao, Netherlands

[21] Appl. No.: 869,982

[22] Filed: Jun. 5, 1997

[30] Foreign Application Priority Data

Jun. 6, 1996 [IT] Italy ................................ MI96A1152

[51] Int. Cl.⁶ .................................................. A61F 13/00
[52] U.S. Cl. ........................................ 424/449; 514/944
[58] Field of Search ............................ 424/449; 514/944

[56] References Cited

U.S. PATENT DOCUMENTS

| | | | |
|---|---|---|---|
| 4,315,925 | 2/1982 | Hussain et al. | 424/239 |
| 4,956,171 | 9/1990 | Chang | 424/449 |
| 4,973,468 | 11/1990 | Chiang | 424/449 |
| 5,023,084 | 6/1991 | Chien et al. | 424/448 |
| 5,120,546 | 6/1992 | Hansen | 424/469 |
| 5,145,682 | 9/1992 | Chien et al. | 424/448 |
| 5,453,279 | 9/1995 | Lee | 424/448 |
| 5,455,042 | 10/1995 | Sakai | 424/443 |

FOREIGN PATENT DOCUMENTS

| | | |
|---|---|---|
| 0 279 977 | 8/1988 | European Pat. Off. . |
| 0 285 563 | 10/1988 | European Pat. Off. . |
| 0 367 431 | 5/1990 | European Pat. Off. . |
| 0 399 432 | 5/1990 | European Pat. Off. . |
| 0 573 133 | 12/1993 | European Pat. Off. . |
| 2518879 | 7/1983 | France . |
| 2 208 147 | 3/1989 | United Kingdom . |
| 90/11064 | 10/1990 | WIPO . |

OTHER PUBLICATIONS

Chien, Yie W., "Developmental Concepts and Practice in Transdermal Therapeutic Systems", *Developmental Concepts and Practice in TTS*, pp. 25–81. Date 1987.

Powers et al., "Pharmacokinetics and pharmacodynamics of transdermal dosage forms of 17β–estradiol: Comparison with conventional oral estrogens used for hormone replacement", American Journal of Obstetrics and Gynecology, Aug. 15, 1985, vol. 152, No. 8, pp. 1099–1106.

Davis et al., "Supersaturated Solution as Topical Drug Delivery Systems", *Pharmaceutical Skin Penetration Enhancement*, pp. 243–267, 1993.

Roberts et al., "Water: The Most Natural Penetration Enhancer", *Pharmaceutical Skin Penetration Enhancement*, Marcel Dekker, Inc., 1993, pp. 1–29.

Brain et al., "Molecular Modeling of Skin Permeation Enhancement by Chemical Agents", *Pharmaceutical Skin Penetration Enhancement*, pp. 389–416, 1993.

Balfour et al., "Transdermal Estradiol: A Review", Drugs 40(4), 1990, pp. 561–582.

Whitehead et al., "Transdermal administration of oestrogen/progestogen hormone replacement therapy", *The Lancet*, vol. 335, Feb. 10, 1990, pp. 310–312.

Birgitte MØllgaard, "Synergistic Effects in Percutaneous Enhancement", *Pharmaceutical Skin Penetration Enhancement*, pp. 229–242, 1993.

*Primary Examiner*—D. Gabrielle Brouillette
*Attorney, Agent, or Firm*—McDermott, Will & Emery

[57] ABSTRACT

Pharmaceutical formulation in the form of a gel suitable for the transdermal administration of an active agent of the class of estrogens or of progestin class or of a mixture of both, comprising:

as permeation enhancers of the above said active agents a combination consisting substantially of an aliphatic alcohol having general formula $CH_3(CH_2)_nCH_2OH$ wherein n=8–16 and of a monoalkylether of diethylene glycol;

as a vehicle or carrier, a combination of an alkanol of 2÷4 C atoms, a glycol and water;

as gelling agent a polymer or copolymer of acrylic acid; a tertiary amine as a thickening and neutralizing agent.

14 Claims, 3 Drawing Sheets

COMPOSITION FOR TRANSDERMAL ADMINISTRATION OF AN ESTROGEN

FIELD OF THE INVENTION

The present invention relates to a novel composition for transdermal administration of an estrogen, a progestin or a mixture thereof. The invention reveals a pharmaceutical formulation with good cosmetic properties and low irritation potential, useful for hormone replacement therapy (HRT) by transdermal route. A formulation that administers 17-β-estradiol and norethindrone acetate, at a permeation rate that would ensure therapeutically effective systemic concentration, containing defined amounts of chemicals that minimize the barrier characteristics of the most uppermost layer of the epidermis and provide sustained permeation rate. Said chemicals are: fatty alcohols such as lauryl alcohol, n-decanol, oleyl alcohol, etc. and diethylene glycol monoethyl ether in a ternary vehicle composite consisting of ethanol, propylene glycol and water.

BACKGROUND OF THE INVENTION

While there are many patents and publications available which relate to the transdermal administration of steroid drugs, and the use of penetration enhancer, the applicant is unaware of any prior art which relates to the enhancer and vehicle composition of a semisolid dosage form disclosed herein and to use such composition in the transdermal administration of estrogen, progestin or a mixture thereof.

The present invention relates to a novel composition based on enhancers combination in a vehicle composite for transdermal administration of steroid hormones alone or mixture thereof. A formulation that provides therapeutically useful concentrations of steroid hormones such as estradiol and norethindrone for hormone replacement therapy.

When the ovaries do not function properly due to age i.e. menopause or disease or have been removed, the consequent lack of endogenous estradiol may produce a number of symptoms, such as hot flushes, pain and increased hypocalcemia which may eventually lead to osteoporosis.

One possibility of avoiding or alleviating these symptoms is by hormone replacement therapy i.e. by prescribing a compensatory doses of estrogen to the patient.

The serum levels of estradiol required for clinical efficacy have been reviewed by Powers between 40–60 pg/ml. This range of values are the physiologic serum levels of the premenopausal women during the early follicular phase.

Various methods or dosage forms are in use or have been proposed for the estradiol replacement therapy e.g. tablets, injectable, implants and transdermal devices (patches or gel) etc.

Oral therapy, using tablets is well accepted by the patient. However estradiol is rapidly metabolized during the liver first pass inactivation generating estrone. Thus, a high dose of estradiol is necessary to achieve clinical appropriate estradiol serum levels and as a consequence, high estrone serum levels are produced above physiological values. Absorption via the gastrointestinal tract results in enhanced delivery of the circulating estrogen to the liver, where much of it is metabolized to inactive conjugates, and only a fraction of the active hormone enter general circulation. The liver responds to this enhanced delivery with increased protein and lipid metabolism, and these activities may carry potential risks.

Examples of these changes include enhanced hepatic synthesis of renin substrates, sex hormone-binding globulin, and changes in cholesterol and lipid lipoprotein metabolism.

The use of parenteral injections and implants or pellets while avoiding the first pass metabolization is much less convenient for the patient, then these dosage forms are not popular.

The estradiol transdermal administration is the cutaneous delivery device which delivers estradiol into the systemic circulation via the stratum corneum at a constant rate. Clinical studies shows beneficial effects of transdermal estradiol on plasma. Gonadotrophins, maturation of the vaginal epithelium, metabolic parameters of bone resorption and menopausal symptoms (hot flushes, sleep disturbance, genitourinary discomfort and mood attention) appear to be comparable to those of oral and subcutaneous estrogens, while the undesirable effects of oral estrogen on hepatic metabolism are avoided (Balfour 1990).

The physicians normally prescribe a progestin combining estrogen to postmenopausal women who have not undergone hysterectomy. Unopposed estrogen cause endometrial hyperstimulation, which lead to irregular vaginal bleeding, endometrial hyperplasia and cancer. Only progestin addition can protect the endometrium while maintaining the beneficial effects of estrogen on symptoms and the skeleton. According to the literature, the transdermal dose of norethindrone acetate required to oppose estrogen hyperstimulation of the endometrium is about 200–300 mcg/day (Whitehead 1990).

Transdermal estradiol must be administered continuously or in 28 day cycle, consisting of three weeks treatment followed by a one week treatment free interval (during which vaginal bleeding may occur). Continuous therapy may be particularly suitable for women who have undergone hysterectomy or those symptoms of estrogen deficiency occur during free intervals.

Additional progestin treatment should be taken by patients with an intact uterus for 10 to 15 consecutive days of each month. Withdrawal bleeding will usually occur at the end of each phase of progestin therapy whether estrogen treatment is cyclical or continuous.

Continuous/combined therapy (continuous estrogen with continuous progestin) has the advantage of not causing withdrawal bleeding.

Transdermal administration of drugs offers several therapeutic and compliance advantages over the more traditional routes of administration. A major drawback of this therapy however, is the limitation of the amount of drug that can be transported across the skin. This limitation is due to several factors. Since the skin is a protective barrier by nature, the rates of transport of most compounds through the skin is quite slow. It is generally accepted that a surface of patch beyond 50–100 sqcm would result in difficulty of application. Therefore the application of a transdermal semisolid dosage form such as a gel, cream, ointment, liquid, etc., augment the patient's compliance and the surface of application can be extended.

In order to overcome the barrier properties of the stratum corneum and facilitate the percutaneous absorption of the active agent, many compounds are described as penetration enhancer, such as, azone, glycol, pyrrolidone, fatty alcohol, fatty acid and ester thereof, etc., mentioned by Møllgaard in "Pharmaceutical Skin Penetration Enhancement", Marcel Dekker, New York 1993, pages 229–242.

EPA 0 367 431 discloses that aliphatic alcohols such as isopropyl alcohol and isobutyl alcohol that are commonly used in topical transdermal formulation thus, enhance the rate of transdermal delivery of steroid drugs.

EP 0 573 133 claims a transdermal device which contains gestodem in combination with one or more estrogens. It is also described the addition of transdermal penetration enhancers.

FR 2 518 879 claims a medicament based of estradiol for postmenopausal treatment. This simple medicament is an hydroalcoholic gel where estradiol is dissolved in the above mentioned vehicles and is appointed to administer estradiol by transdermal route.

EPA 0 279 977 describes a transdermal device for administering progesterone and an estradiol ester alone or in combination, utilizing a polymer matrix which has the drug(s) with a penetration enhancer such as sucrose monococoate, glycerol monooleate, sucrose monolaurate, glycerol mnolaureate, etc.

U.S. Pat. No. 5,023,084 claims a transdermal estrogen/progestin device comprising a polymeric layer made from polymer adhesive such as polyacrylic, silicone or other suitable polymer adhesives and decyl alcohol as penetration enhancer.

GB 2 208 147 A discloses a transdermal reservoir type with controlled membrane for the administration of estrogen and progestin, containing ethanol as an agent that enhances the percutaneous absorption.

WO 90/11 064 discloses a skin penetration enhancer composition for estrogen and progestin or a mixture thereof. The composition contains diethylene glycol monoethyl or monomethyl ether in addition to propylene glycol monolaurate, methyl laurate or the like.

None of the above mentioned inventions or publications report a study of lauryl alcohol together with diethylene glycol monoethyl ether in a ternary vehicle composite in a semisolid dosage form, designed to administer estradiol and norethindrone acetate simultaneously by the transdermal route.

One object of the present invention is to obtain a transdermal formulation that could deliver, at controlled rates, both an estrogen and progestin combined with appropriate permeation enhancers. This is very important since it is well known that transdermal permeability is mainly influenced by both physicochemical properties of the permeants and by the interaction of the permeants with the enhancers. Therefore a given enhancer could prove to be very adequate for an hormone and simultaneously would not increase the permeability of the other hormone. This is well illustrated by Chien, in its chapter on "Development Concepts and Practice in Transdermal Therapeutic Systems" in Transdermal Therapeutic Systemic Medications, Marcel Dekker Inc., New York, 1987, pages 25–81, who state that a penetration enhancer increases the permeation of different compound to different degree.

There has not been known an enhancer or combination thereof which shows the transdermal penetration enhancement effect for any active agent or drug. As an example we can quote results of this author as therein below indicated:

Enhancement of Skin Permeability of Various Drugs by Different Types of Enhancer

| Drugs | Enhancement factor[a] | | | |
| --- | --- | --- | --- | --- |
| | Propyl myristate | Propyl oleate | Azone | Decylmethyl sulfoxide |
| Progesterone | 4.56 | 5.36 | 5.96 | 11.04 |
| Estradiol | 9.33 | 14.62 | 20.17 | 12.59 |
| Hydrocortisone | 4.57 | 5.01 | 61.3 | 25.23 |
| Indomethacin | 3.77 | 4.67 | 14.49 | 15.67 |

[a]Enhancement factor = (Normalized skin permeation rate) with enhancer/(Normalized skin permeation rate) without enhancer.

Additionally, another argument in favor of our position is sustained when the results reported by Chien are analyzed. He published the dependence of the enhancement factor for the skin permeation of progesterone on the alkyl chain length of saturated fatty acid in "Transdermal Therapeutic Systemic Medications". He found the major enhancement effect using caproic acid (C8), however the same author discloses in U.S. Pat. No. 5,145,682 that the better enhancer for estradiol is decanoic acid (C10). These results lead us to attain the same conclusion of Chien in "Transdermal Controlled Systemic Medications", Marcel Dekker, New York 1987, pages 25–81, that concludes that the efficacy of skin penetration enhancer for a specific active agent, is function of the type, concentration and, how the penetration enhancer release from the devices.

The prior art presented herein clearly prove that at least for steroid compounds, as shown in the present patent application, there is no such an universal penetration enhancer composition and the adequate permeation rate across the skin can be achieved only by testing different types of compounds at different concentrations. Although prior art was useful for the theoretical approach, the results emerged from the careful investigation of multiple variables.

SUMMARY OF THE INVENTION

It has been surprisingly discovered that it is possible to achieve a therapeutically effective, sustained and controlled penetration rate of the steroid hormones into the skin with the aid of the inventive means.

A semisolid dosage form which provides a therapeutically effective transdermal delivery of estrogen or synthetic progestin, or mixture thereof, is claimed:

It has been discovered surprisingly that the formulation discloses herein, exerts higher permeation rate under non occlusive conditions. On the contrary, the permeation rate from Oestrogel$^R$. (Besins Iscovesco) exhibits higher values when the in vitro permeation studies are conducted in occlusive condition.

Surprisingly it has discovered that in the administration of norethindrone acetate, the lauryl alcohol acts as the most adequate enhancer. Thus, higher permeation ratio norethindrone acetate/estradiol is achieved using lauryl alcohol at the same concentration ratio norethindrone acetate/estradiol in the formulation.

It has found that when estradiol and norethindrone acetate are combined, an interference in the permeation process occurs between both active agents.

Surprisingly, it has found that lauryl alcohol is a good penetration enhancer for early times and diethylene glycol monoethyl ether is a good penetration enhancer for late times.

DETAILED DESCRIPTION OF THE INVENTION

An objective of this invention is to provide a formulation which shows adequate transdermal penetration enhancement effect for many steroid compounds such as estradiol, norethindrone or a mixture thereof.

The main objective of this invention is to provide a gel which shows adequate and effective transdermal penetration enhancement for estradiol or norethindrone acetate, or a mixture thereof. Accordingly, it is an object of the present invention to provide a skin permeation enhancer composition comprising of a first component that is a fatty alcohol given by the formula CH3-(CH2)n-CH2OH, in which n is an integer from 8 to 16, preferably 8 to 12, most preferably 10; and a second component that is an monoalkyl ether of diethylene glycol, preferably diethylene glycol monoethyl ether or diethylene glycol monomethyl ether and most preferably diethylene glycol monoethyl ether, in a vehicle or carrier composition, integrated by an alkanol having from 2 to 4 C atoms, preferably ethanol; a polyalcohol, preferably propylene glycol and water.

It has been discovered that in a transdermal formulation comprising estradiol and norethindrone acetate as active agents; lauryl alcohol and diethylene glycol monoethyl ether as penetration enhancers, in a ternary vehicle composite comprised of ethanol, propylene glycol and water, using a polymer or copolymer of acrylic acid, preferably Carbomer $^R$ as gelling forming, provides therapeutically effective serum concentration of both hormones throughout a 24 hours period. As it is concludes when a bioavailability study of the above mentioned formulation was carried out in postmenopausal women volunteers.

Although the mechanism of such stratum corneum effect in the present invention is not fully clear by the scientific knowledge up to now, it can be understood as follows:

The fatty alcohol is mainly distributed to the stratum corneum because of its lipophilicity and interacts with the stratum corneum lipids.

The diethylene glycol monoethyl ether dissolves both an hydrophilic and a lipophilic active agents therein and facilitates the penetration of the active agents to the skin.

A lower monohydric alcohol, such as ethanol, also has a function to increase the stratum corneum liquid fluidity or a function to extract lipids from the stratum corneum.

Propylene glycol, a widespread pharmaceutical vehicle, acts as a cosolvent of the drugs hence increase the solubility of the active agent in the formulation and solvated the intracellular keratin of the stratum corneum and thus enhanced drug mobility.

Water serves to augment the solubility of a hydrophilic active agent in the formulation and accelerate the release of lipophilic active agent from the formulation in addition to a skin hydration.

A polymer or copolymer of acrylic acid, such as Carbomer $^R$ acts as a gelling forming and facilitates the release of lipophilic active agent and penetration enhancer.

A tertiary amine, such as triethanolamine, has the function to thicken and neutralize the system.

This invention relates to a novel composition for transdermal application to humans and methods for providing therefrom a controlled dosage of estradiol and norethindrone acetate. The novel composition comprises estradiol and norethindrone acetate or a mixture thereof in a gel dosage form optimized for the adequate permeation rate so that the concentration of drugs in the blood serum of the patient is maintained within levels desirable for optimum clinical efficacy.

The therapeutically effective daily dose is about 40–50 mcg/day of estrogen based on 17-β-estradiol and is about 200–250 mcg/day of progestin based on norethindrone acetate on the basis of the prior art. (Powers 1985 and Whitehead 1990).

Surprisingly when we combined estradiol and norethindrone acetate an interference in the permeation process was found. This interference was not mentioned in prior art that discloses about combined transdermal administration of estrogen and progestin.

It is by no means obvious that a particular synthetic progestin could be effectively administered transdermally with or without a penetration enhancer, and essentially in a sufficient amount to counteract the estrogen endometrial hyperplasia.

Use of combination of two or more of the skin penetration enhancer compounds frequently result in superior effects, such as greater transdermal absorption, but it is presently herein that the combination of penetration enhancers resulted in controlled and sustained percutaneous absorption of the hormones throughout a 24 hs. period.

The scientific literature states that a true synergistic effect is achieved when the combination of penetration enhancers elicits a greater effect than the individual components used alone.

It has found that lauryl alcohol exerts higher enhancement factor in the early times, while it has found that diethylene glycol monoethyl ether enhances the permeation rates of the hormones in the later times. Moreover a mixture of the above mentioned penetration enhancers conduct us to provide adequate and sustained hormone serum levels throughout a 24 hs. period, as it is demonstrated in the bioavailability study in postmenopausal women reported herein.

In the preferred embodiment of the present invention, the estradiol and norethindrone acetate are dissolved in said gel dosage form as pharmacologically active agents in amount comprised from 0.02 to 0.09% (w/w), preferably 0.04 to 0.07% (w/w) and most preferably 0.06% (w/w) for estradiol; and from 0.30 to 1.50% (w/w), preferably 0.60 to 1.20% (w/w) and most preferably 1.20% (w/w) for norethindrone acetate. The fatty alcohol selected, lauryl alcohol, is comprised from 0.40 to 6.00% (w/w), preferably 1.00 to 4.00% (w/w) and most preferably 2.00% (w/w) and diethylene glycol monoethyl ether is comprised from 1.00 to 15.00% (w/w), preferably 2.50 to 10.00% (w/w) and most preferably 5.00% (w/w).

The active agents and the compounds which enhances the hormones penetration rate are dissolved in a ternary vehicle composite integrated by an alkanol having 2–4 C atoms preferably ethanol; a polyalcohol, preferably propylene glycol and purified water.

Thus, the finished formulation comprises: estradiol in amount from 0.02 to 0.09% (w/w), preferably 0.04 to 0.07% (w/w) and most preferably 0.06% (w/w); norethindrone acetate from 0.30 to 1.50% (w/w), preferably 0.60 to 1.20% (w/w) and most preferably 1.20% (w/w); lauryl alcohol from 0.40 to 6.00% (w/w), preferably 1.00 to 4.00% (w/w) and most preferably 2.00% (w/w); diethylene glycol monoethyl ether from 1.00 to 15.00% (w/w), preferably 2.50 to 10.00% (w/w) and most preferably 5.00% (w/w); ethanol in amount from 20.00 to 65.00% (w/w), preferably 30.00 to 55.00% (w/w) and most preferably 44.49% (w/w); propylene glycol from 1.00 to 12.00% (w/w), preferably 3.00 to 9.00% (w/w) and most preferably 6.00% (w/w) and water from 20.00 to 65.00% (w/w), preferably 30.00 to 55.00% (w/w) and most preferably 39.45% (w/w). Finally, the other components to complete the formulation are: carbomer in amount from 0.50 to 4.00% (w/w), preferably 1.00 to 2.50% (w/w) and most preferably 1.20% (w/w); Triethanolamine in amount from 0.05 to 1.00% (w/w), preferably 0.10 to 0.60% (w/w) and most preferably 0.40% (w/w) and flavouring agents in amount from 0.05 to 0.50% (w/w), preferably 0.10 to 0.30% (w/w) and most preferably 0.20% (w/w).

Optionally the formulation can comprise E.D.T.A. (ethylenediamminotetraacetic acid) in amount up to 0.2% by weight on the total weight of the formulation, as an antioxidant additive.

The percentage is based on the total weight of the said gel dosage form.

DEFINITION OF TERMS

"Penetration enhancement" or "permeation enhancement" as used herein relates to an increase in the permeability of skin to a pharmacologically active agent, i.e., so as to increase the rate at which the drug permeates through the skin and enters the bloodstream. The enhanced permeation effected through the use of such enhancers, and in particular, through the use of the enhancer composition of the present invention, can be observed by measuring the rate of diffusion of drug through animal or human skin using a diffusion cell apparatus as described in the examples herein.

An "effective" or an "adequate" permeation enhancer as used herein means a permeation enhancer that will provide the desired increase in skin permeability and correspondingly, the desired depth of penetration, rate of administration, and amount of drug delivered.

By "transdermal" delivery, applicants intend to include both transdermal (or "percutaneous") and transmucosal administration, i.e., delivery by passage of a drug through the skin or mucosal tissue and into the bloodstream.

"Carriers" or "vehicles" as used herein refer to carrier materials suitable for transdermal drug administration, and include any such materials known in the art, e.g., any liquid, gel, solvent, liquid diluent, solubilizer, or the like, which is non toxic and which does not interact with other components of the composition in a deleterious manner. Examples of suitable vehicles for use herein include water, alcohols, polyalcohols, and glycols.

By the term "pharmacologically active agent" or "drug" as used herein is meant any chemical material or compound suitable for transdermal or transmucosal administration which induces a desired systemic effect.

By "therapeutically effective" amount of a pharmacologically active agent is meant a non toxic but sufficient amount of a compound to provide the desired therapeutic effect.

Figure 3:
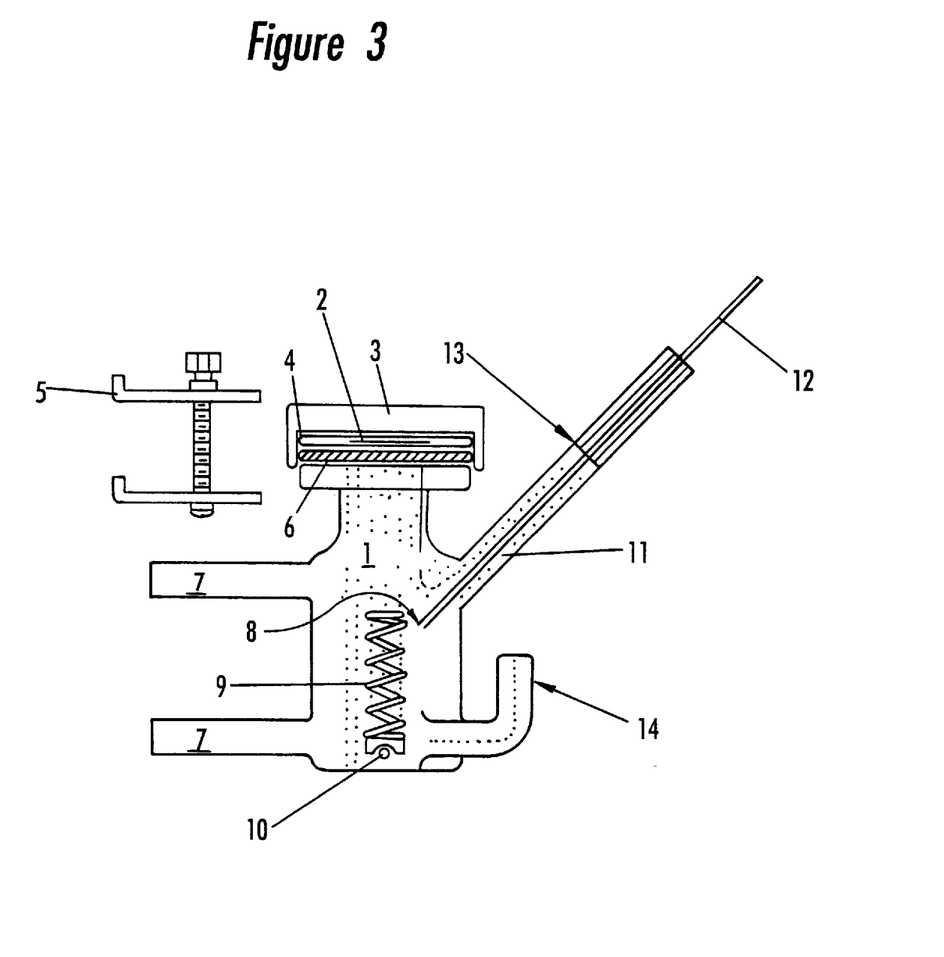
FIG. 3 an apparatus "Hanson P/N 57-VC" (vertical diffusion cell) is schematically represented 3 wherein:
1=cell receptor
2=donor chamber (dosage area)
3=top plate
4=dosage wafer
5=clamp 6=membrane
7=water jacket
8=sample point
9=stirring helix
10=magnetic stirrer
11=sample tube
12=sample probe from microette
13=cell level line
14=media replace tube Typical cell dimensions are: orifice 15 mm, volume 7 ml.

The term "occlusive condition" used for the experimental tests carried out with the apparatus described in FIG. 3, means that the donor chamber (2) of the diffusion is closed by the top plate (3) i.e. not in communication with the external air. On the contrary the term "non occlusive condition" means that the top plate (3) has a hole allowing the free interaction between the formulation to be tested and the external air permitting the evaporation of the volatile solvents.

EXAMPLES

The following examples are in illustration of the invention and are not intended to be limiting.

Example 1

The estrogen hormone is preferably the naturally occurring estrogen 17-β-estradiol. Other estrogenic steroid hormones can be used in partial or complete replacement of 17-β-estradiol. For example an ester which is biologically compatible and can be absorbed effectively transdermally. The estradiol esters can be, illustratively estradiol-3,17-diacetate; estradiol-3-acetate; estradiol-17-acetate; estradiol-3,17-divalerate; estradiol-3-valerate; estradiol-17-valerate; 3-mono, 17-mono and 3,17-dipropionate esters, corresponding cypionate, heptanoate, benzoate and the like esters; ethynil estradiol; estrone and other estrogenic steroids and derivatives thereof that are possible to administer by transdermal route. Combinations of the above mentioned steroids can be used.

It is presently preferred norethindrone acetate as progestin. Other progestin can be used from norethindrone, norgestimate, medroxiprogesterone, progesterone, progesterone acetate, norgestrel, chlormadinone, gestadene etc.

Lauryl alcohol and diethylene glycol monoethyl ether are preferably the permeation enhancers compounds.

Other enhancing agents can be used instead of lauryl alcohol. Other suitable agents such as n-decanol, lauric acid, oleyl alcohol, etc., could be suggested to those skilled in art in view of the disclosures herein.

A gel containing estradiol 0.06% (w/w), norethindrone acetate 1.20% (w/w) (ratio norethindrone acetate/estradiol= 20:1), lauryl alcohol 2.00% (w/w), diethylene glycol monoethyl ether 5.00% (w/w), ethanol 44.53% (w/w), propylene glycol 5.99% (w/w), purified water 39.43% (w/w), carbomer 1.20% (w/w), triethanolamine 0.39% (w/w), flavouring agents 0.20% (w/w) was prepared in a 250 ml vessel, dispersing the carbomer in the total quantity of purified water by stirring at room temperature with a mixing equipment at 300 rpm to avoid lumps and air bubble entrapment. Carbomer was slowly poured and sprinkled into the water. After 1 hour, the propylene glycol was added with continuous mixing to homogenize. Meanwhile, the ethanolic phase was prepared in another vessel, dissolving estradiol, norethindrone acetate, lauryl alcohol, diethylene glycol monoethyl ether and the flavouring agents in the total quantity of ethanol. Then, the ethanolic phase was poured into the water phase and it was stirred at 300 rpm until homogeneity. Finally, while stirring, the triethanolamine was added.

Example 2

A gel containing estradiol 0.04% (w/w), norethindrone acetate 0.60% (w/w), (ratio norethindrone acetate/estradiol= 15:1), lauric acid 1.00% (w/w), diethylene glycol monoethyl ether 5.01% (w/w), ethanol 47.16% (w/w), propylene glycol 4.64% (w/w), purified water 40.12% (w/w), carbomer 1.20% (w/w), triethanolamine 0.23% (w/w) prepared according the technique described in example 1.

Example 3

A gel containing estradiol 0.015% (w/w), norethindrone acetate 0.450% (w/w), (ratio norethindrone acetate/ estradiol=30:1), lauric acid 1.00% (w/w), diethylene glycol monoethyl ether 5.07% (w/w), ethanol 43.54% (w/w), propylene glycol 4.99% (w/w), purified water 43.54% (w/w), carbomer 1.20% (w/w), triethanolamine 0.20% (w/w) prepared according the technique described in example 1.

Example 4

A gel containing lauryl alcohol instead of lauric acid, wherein the composition is: estradiol 0.015% (w/w), norethindrone acetate 0.45% (w/w), (ratio norethindrone acetate/estradiol=30:1), lauryl alcohol 1.00% (w/w), diethylene glycol monoethyl ether 5.07% (w/w), ethanol 43.52% (w/w), propylene glycol 4.99% (w/w), purified water 43.52% (w/w), carbomer 1.20% (w/w), triethanolamine 0.24% (w/w) prepared according the technique described in example 1.

Example 5

A gel containing estradiol 0.06% (w/w), ethanol 48.80% (w/w), propylene glycol 6.06% (w/w), purified water 43.28% (w/w), carbomer 1.20% (w/w), triethanolamine 0.40% (w/w), flavouring agents 0.20% (w/w) prepared according the technique described in example 1.

Example 6

A gel containing norethindrone acetate 1.20% (w/w), ethanol 48.22% (w/w), propylene glycol 6.06% (w/w), purified water 42.69% (w/w), carbomer 1.20% (w/w), triethanolamine 0.43% (w/w), flavouring agents 0.20% (w/w) prepared according the technique described in example 1.

Example 7

A gel containing estradiol 0.06% (w/w), norethindrone acetate 1.20% (w/w), (ratio norethindrone acetate/estradiol=20:1), ethanol 48.19% (w/w), propylene glycol 5.98% (w/w), purified water 42.72% (w/w), carbomer 1.20% (w/w), triethanolamine 0.43% (w/w), flavouring agents 0.22% (w/w) prepared according the technique described in example 1.

Example 8

A gel containing basically the same formulation of example 5, but with the addition of lauryl alcohol and diethylene glycol monoethyl ether as penetration enhancer. Thus the composition is:

Estradiol 0.06% (w/w), lauryl alcohol 2.00% (w/w), diethylene glycol monoethyl ether 5.00% (w/w), ethanol 45.22% (w/w), propylene glycol 5.96% (w/w), purified water 39.96% (w/w), carbomer 1.20% (w/w), triethanolamine 0.40% (w/w), flavouring agents 0.20% (w/w) prepared according the technique described in example 1.

Example 9

A gel containing basically the same formulation of example 6, but with the addition of lauryl alcohol and diethylene glycol monoethyl ether as penetration enhancer. Thus the composition is:

Norethindrone acetate 1.20% (w/w), lauryl alcohol 2.01% (w/w), diethylene glycol monoethyl ether 5.02% (w/w), ethanol 44.52% (w/w), propylene glycol 6.00% (w/w), purified water 39.46% (w/w), carbomer 1.20% (w/w), triethanolamine 0.39% (w/w), flavouring agents 0.20% (w/w) prepared according the technique described in example 1.

Example 10

A gel containing estradiol 0.06% (w/w), norethindrone acetate 1.20% (w/w), (ratio norethindrone acetate/estradiol=20:1), lauryl alcohol 2.00% (w/w), ethanol 50.32% (w/w), purified water 44.61% (w/w), Carbomer 1.20% (w/w), triethanolamine 0.40% (w/w), flavouring agents 0.21% (w/w) prepared according the technique described in example 1.

Example 11

A gel containing estradiol 0.06% (w/w), norethindrone acetate 1.21% (w/w), (ratio norethindrone acetate/estradiol=20:1), diethylene glycol monoethyl ether 5.02% (w/w), ethanol 48.60% (w/w), purified water 43.33% (w/w), carbomer 1.20% (w/w), triethanolamine 0.38% (w/w), flavouring agents 0.20% (w/w) prepared according the technique described in example 1.

Example 12

A gel containing estradiol 0.03% (w/w), norethindrone acetate 0.60% (w/w), (ratio norethindrone acetate/estradiol=20:1), diethylene glycol monoethyl ether 5.00% (w/w), ethanol 45.83% (w/w), propylene glycol 6.11% (w/w), purified water 40.63% (w/w), Carbomer 1.20% (w/w), triethanolamine 0.40% (w/w), flavouring agents 0.20% (w/w) prepared according the technique described in example 1.

Example 13

A gel containing basically the same formulation of example 12, but with the addition of n-decanol (n-decylalcohol) as penetration enhancer. Thus the composition is:

Estradiol 0.03% (w/w), norethindrone acetate 0.60% (w/w), (ratio norethindrone acetate/estradiol=20:1), n-decanol 1.00% (w/w), diethylene glycol monoethyl ether 5.0% (w/w), ethanol 45.35% (w/w), propylene glycol 6.03% (w/w), purified water 40.21% (w/w), carbomer 1.20% (w/w), triethanolamine 0.40% (w/w), flavouring agents 0.17% (w/w) prepared according the technique described in example 1.

Example 14

A gel containing basically the same formulation of example 12, but with the addition of oleyl alcohol as penetration enhancer. Thus the composition is:

Estradiol 0.03% (w/w), norethindrone acetate 0.60% (w/w), (ratio norethindrone acetate/estradiol=20:1), oleyl alcohol 1.00% (w/w), diethylene glycol monoethyl ether 5.00% (w/w), ethanol 45.95% (w/w), propylene glycol 5.01% (w/w), purified water 40.77% (w/w), carbomer 1.22% (w/w), triethanolamine 0.22% (w/w), flavouring agents 0.20% (w/w) prepared according the technique described in example 1.

Example 15

A gel containing basically the same formulation of example 12, but with the addition of lauryl alcohol as penetration enhancer. Thus the composition is:

Estradiol 0.03% (w/w), norethindrone acetate 0.60% (w/w), (ratio norethindrone acetate/estradiol=20:1), lauryl alcohol 2.0% (w/w), diethylene glycol monoethyl ether 5.0% (w/w), ethanol 45.43% (w/w), propylene glycol 5.02% (w/w), purified water 40.29% (w/w), carbomer 1.20% (w/w), triethanolamine 0.20% (w/w), flavouring agents 0.21% (w/w) prepared according the technique described in example 1.

Example 16

A gel containing estradiol 0.06% (w/w), norethindrone 0.50% (w/w), (ratio norethindrone/estradiol about 8,3:1), lauryl alcohol 1.99% (w/w), diethylene glycol monoethyl ether 4.98% (w/w), ethanol 44.75% (w/w), propylene glycol 6.31% (w/w), purified water 39.62% (w/w), carbomer 1.20% (w/w), triethanolamine 0.40% (w/w), flavouring agents 0.19% (w/w) prepared according the technique described in example 1.

Example 17

A gel containing estradiol 0.061% (w/w), medroxiprogesterone acetate 0.297% (w/w), (ratio medroxiprogesterone acetate/estradiol about 4,8:1), lauryl alcohol 1.98% (w/w), diethylene glycol monoethyl ether 5.10% (w/w), ethanol 44.98% (w/w), propylene glycol 5.96% (w/w), purified water 39.86% (w/w), carbomer 1.20% (w/w), triethanolamine 0.39% (w/w), flavouring agents 0.18% (w/w) prepared according the technique described in example 1.

IN VITRO PERMEATION STUDIES

Furthermore, in vitro permeation experiments through abdominal guinea pig skin was made using the diffusion chamber that is schematically shown in FIG. 3.

Female guinea pigs, 8 to 16 months of age were shaved on their abdominal skin 72 hs. before sacrifice by cervical dislocation. Only animals that showed absence of lesions were used. A section of full thickness abdominal skin was surgically excised and mounted between the sections of a vertical diffusion cell having 1.77 sqcm of surface area, the epidermal facing up. A given amount of the pharmaceutical formulations exemplified above were spread over the epidermal layer whilst the dermal layer contact with a solution of sodium lauryl sulfate (SDS), at 34° C. The appearance of the hormones in the inferior compartment (receptor phase) was monitored taking samples at given times and measured afterwards using a high performance liquid chromatography (HPLC) method.

The experiments were conducted in two different conditions: in occlusive condition with a glass stopper, which avoid the evaporating of the volatile solvents, and in non occlusive condition, whereas the stopper used allow the evaporation of the volatile solvents.

The following tables illustrate the in vitro permeation results.

TABLE I

Occlusive vs. Non Occlusive Conditions

| | | Guinea Pig Skin | |
|---|---|---|---|
| Example | Condition | Estradiol Permeated mcg/sqcm/ 24 h ± SEM (n = 4) | Norethindrone Acetate Permeated mcg/sqcm/ 24 h ± SEM (n = 4) |
| 2 | Non occlusive | 19.7 ± 3.5 | 103.9 ± 23.8 |
| 2 | Occlusive | 10.4 ± 0.5 | 82.6 ± 8.3 |
| Oestrogel ® | Non Occlusive | 0.4 ± 0.4 | |
| Oestrogel ® | Occlusive | 36.5 ± 6.3 | |

In Table I are summarized the results obtained with the example 2 and with Oestrogel. (Besins Iscovesco) under occlusive and non occlusive conditions.

The results obtained with Oestrogel. were about 90 (ninety) folds higher during the experimentation under occlusive condition. However it has found surprisingly that our example show higher permeation values for 17-β-estradiol and norethindrone acetate under non occlusive condition.

We could postulate that the behavior of our formulation was due to the addition of several phenomenon. These factors are listed as follow:

The formulation is able to replenish or cram the normal irregularities of the epidermis. Thus a reservoir of vehicles was generated, which enhanced the percutaneous absorption of the compounds, even if all the ethanol was evaporated off.

It is likely that our formulation take advantages of supersaturation. In alcoholic lotions and gels, the effects are predictable but for our more complex system, loss of volatile solvent (alcohol) lead to increase thermodynamic activity in the residual vehicles, by virtue of generating a supersaturated solution (Davis and Hadgraft in "Pharmaceutical Skin Penetration Enhancement", Marcel Dekker, New York 1993).

Other phenomena could be the capability to produce an invisible occlusive film that may diminish the transepidermal water loss and may increment the water content of the epidermis or the state of hydration of the stratum corneum. An increase in water content results in an increased elasticity and permeability of stratum corneum, whereas reducing the water content will lead to an opposite effect (Roberts and Walker in "Pharmaceutical Skin Penetration Enhancement", Marcel Dekker, New York 1993).

TABLE II

Enhancing Effect of Lauryl Alcohol Comparing with Lauric Acid in Occlusive Condition

| | | Guinea Pig Skin | |
|---|---|---|---|
| Example | Enhancer | Estradiol Permeated mcg/sqcm/ 24 h ± SEM (n = 4) | Norethindrone Acetate Permeated mcg/sqcm/ 24 h ± SEM (n = 4) |
| 4 | Lauryl Alcohol 1% | 6.3 ± 0.7 | 166.6 ± 19.6 |
| 3 | Lauric Acid 1% | 6.8 ± 0.9 | 86.8 ± 16.8 |

In Table II are depicted the results obtained using lauryl alcohol and lauric acid as permeation enhancer.

Contrarily to the supposition of Brian and Walters in "Pharmaceutical Skin Penetration Enhancement", Marcel Dekker, New York 1993, that assumed that lauric acid is better enhancer than lauryl alcohol, by virtue of the results completed for naloxone. In our case it has found that both enhancers above mentioned achieve the same enhancement factor for estradiol, however surprisingly for norethindrone acetate the rate of permeation reached using lauryl alcohol was two folds higher. These results confirm our hypothesis that universal enhancer does not exist.

Based upon these results we could estimate that our formulation with lauryl alcohol is able to administer in vivo higher permeation ratio norethindrone/estradiol with the same concentration ratio norethindrone acetate/estradiol in the formulation.

TABLE III

Permeation Interaction Between Estradiol and Norethindrone Acetate
with and without Enhancers in Occlusive Condition Guinea Pig Skin

| Example | Active Agents | Lauryl Alcohol and Diethylene Glycol Monoethyl Ether as Enhancers | Estradiol Permeated mcg/sqcm/24 h ± SEM (n = 4) | Norethindrone Acetate Permeated mcg/sqcm/24 h ± SEM (n = 4) |
|---|---|---|---|---|
| 5 | E2 | NO | 18.7 ± 2.2 | |
| 6 | NETA | NO | | 70.6 ± 11.0 |
| 7 | E2 and NETA | NO | 8.9 ± 2.3 | 76.5 ± 12.8 |
| 8 | E2 | YES | 18.6 ± 1.5 | |
| 9 | NETA | YES | | 83.1 ± 5.8 |
| 1 | E2 and NETA | YES | 9.6 ± 1.4 | 127.3 ± 16.9 |

E2 = estradeiol
NETA = norethindrone acetate

In Table III are depicted the in vitro permeation results obtained with examples 5 (estradiol only), 6 (norethindrone acetate only) and 7 (norethindrone acetate and estradiol) all the examples previously mentioned without enhancers and the examples 8 (estradiol only), 9 (norethindrone acetate only) and 1 (norethindrone acetate and estradiol) containing penetration enhancers.

These results clearly indicate the existence of an interference between the hormones in the permeation process, because the 17-βestradiol permeated from the combination gel is considerable less than the 17-β-estradiol permeated from an estradiol gel. The norethindrone acetate permeated from the norethindrone acetate gel and from the combination gel are not significant different when not enhancer are included in the formulation, but surprisingly it has discovered a significant increase in the norethindrone acetate permeated values from the combination gel when penetration enhancers are included in the formulation.

TABLE IV

Effect of the Enhancers Composition in Occlusive Condition
Guinea Pig Skin

| | | Estradiol Flux mcg/sqcm/h ± SEM (n = 4) | | | Norethindrone Acetate Flux mcg/sqcm/h ± SEM (n = 4) | | |
|---|---|---|---|---|---|---|---|
| Example | Enhancer | 8 h | 16 h | 24 h | 8 h | 16 h | 24 h |
| 10 | Lauryl Alcohol 2.0% | 0.23 ± 0.02 | 0.47 ± 0.02 | 0.22 ± 0.06 | 1.60 ± 0.23 | 4.69 ± 0.53 | 3.79 ± 0.80 |
| 11 | Diethylene Glycol Monoethyl Ether 5.0% | 0.00 ± 0.00 | 0.57 ± 0.22 | 0.44 ± 0.10 | 0.42 ± 0.23 | 5.73 ± 3.10 | 6.58 ± 1.74 |
| 1 | Lauryl Alcohol 2.0% and Diethylene Glycol Monoethyl Ether 5.0% | 0.15 ± 0.09 | 0.59 ± 0.04 | 0.46 ± 0.07 | 2.38 ± 0.52 | 7.55 ± 0.99 | 5.98 ± 0.99 |

In table IV it is shown the enhancer composition effect. It has found that lauryl alcohol is a good penetration enhancer at early time (8 hs), and diethylene glycol monoethyl ether is a excellent penetration enhancer at late times (16, 24 hs). Furthermore the association of lauryl alcohol and diethylene glycol monoethyl ether preferred in the present patent application provides sustained enhancement factor throughout a 24 hs period.

TABLE V

Effect of different enhancers in Occlusive Condition

Guinea Pig Skin

| Example | Enhancer | Estradiol Permeated mcg/sqcm/24 h ± SEM (n = 3) | Norethindrone Acetate Permeated mcg/sqcm/24 h ± SEM (n = 3) |
|---|---|---|---|
| 12 | Diethylene Glycol Monoethyl Ether 5.0% | 5.15 ± 2.50 | 35.78 ± 0.72 |
| 13 | n-Decanol 1.0% and Diethylene Glycol Monoethyl Ether 5.0% | 5.32 ± 0.45 | 84.63 ± 22.13 |

TABLE V-continued

Effect of different enhancers in Occlusive Condition

Guinea Pig Skin

| Example | Enhancer | Estradiol Permeated mcg/sqcm/24 h ± SEM (n = 3) | Norethindrone Acetate Permeated mcg/sqcm/24 h ± SEM (n = 3) |
|---|---|---|---|
| 14 | Oleyl Alcohol 1.0% and Diethylene Glycol Monoethyl Ether 5.0% | 9.02 ± 0.48 | 124.01 ± 12.97 |
| 15 | Lauryl Alcohol 2.0% and Diethylene Glycol Monoethyl Ether 5.0% | 8.71 ± 1.32 | 161.33 ± 56.00 |

In Table V are depicted the in vitro permeation results obtained with four formulations containing in its enhancer composition diethylene glycol monoethyl ether only (example 12), diethylene glycol monoethyl ether and n-decanol (example 13), diethylene glycol monoethyl ether and oleyl alcohol (example 14) and diethylene glycol monoethyl ether and lauryl alcohol (example 15).

Comparing the results obtained with examples 12 and 13, it has found that diethylene glycol monoethyl ether only and diethylene glycol monoethyl ether with the addition of n-decanol achieve the same enhancement factor for estradiol, however, for norethindrone acetate the rate of permeation reached using n-decanol was greater.

Comparing the results obtained with examples 14 and 15, it has found that diethylene glycol monoethyl ether with the addition of oleyl alcohol and diethylene glycol monoethyl ether with the addition of lauryl alcohol achieve the same enhancement factor for estradiol, however, for norethindrone acetate the rate of permeation reached using lauryl alcohol was greater.

These results support our previous hypothesis that universal enhancer does not exist.

The results obtained with examples 12, 13, 14 and 15 clearly shows that lauryl alcohol has the highest enhancement factor for norethindrone acetate, and likewise oleyl alcohol reaches the highest enhancement factor for estradiol.

TABLE VI

Permeation of Norethindrone and Medroxiprogesterone as Progestins

Guinea Pig Skin

| Example | Estradiol Permeated mcg/sqcm/24 h ± SEM (n = 3) | Norethindrone Permeated mcg/sqcm/24 h ± SEM (n = 3) | Medroxiprogesterone acetate Permeated mcg/sqcm/24 h ± SEM (n = 3) |
|---|---|---|---|
| 16 | 14.74 ± 2.08 | 184.50 ± 17.65 | — |
| 17 | 19.25 ± 1.48 | — | 85.80 ± 5.06 |

In Table VI it is shown the in vitro permeation results obtained using the examples 16 and 17. These examples uses estradiol in combination with norethindrone and medroxiprogesterone acetate as progestins respectively.

17-β-ESTRADIOL AND NORETHINDRONE ACETATE BIOAVAILABILITY IN POSTMENOPAUSAL WOMEN

The estradiol and norethindrone acetate permeation rate achieved with the transdermal formulation or composition presented herein, was evaluated "in vivo" by measuring the estradiol and norethindrone serum levels in 8 postmenopausal women, applying one daily dose of 5 gr. of the transdermal formulation described in example 1, over the arms, forearms and shoulders. The duration of the study was 3 days, thus 3 dose application were applied. Blood samples were taken at 0 h (basal value), 2, 6, 12, 24, 30, 36, 48, 54, 60, and 72 hs after the initiation of the study. Estradiol and norethindrone serum levels were determined by time-resolved fluoroimmunoassay and by enzyme immunoassay respectively.

Figure 1:
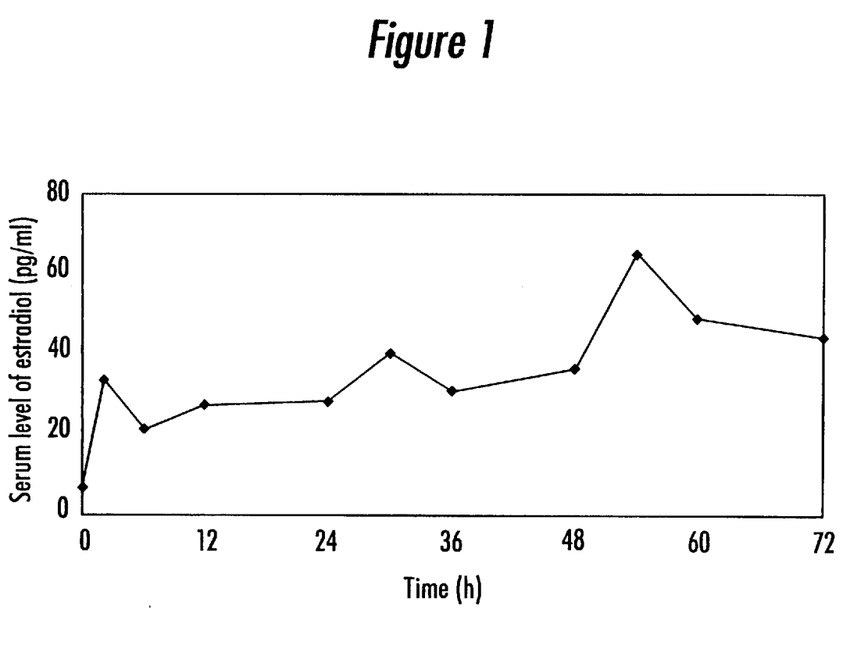
In FIG. 1 there are represented in diagram the experimentally tested values of estradiol serum level versus time, reported in table VII, obtained by use of example 1 transdermal formulation.
Figure 2:
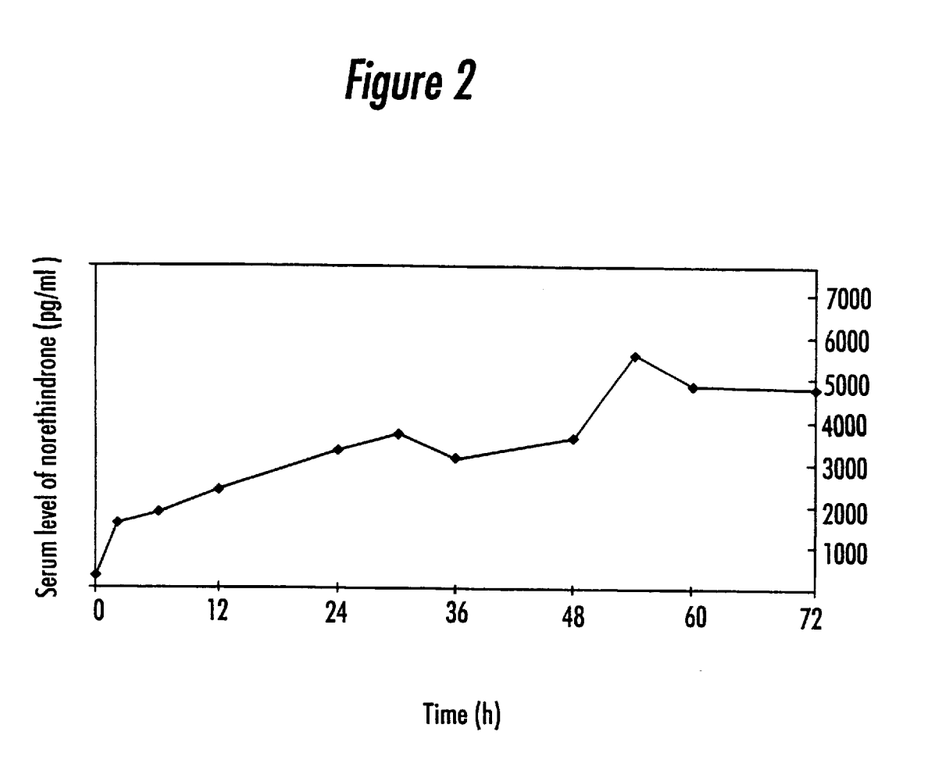
In FIG. 2 there are represented in diagram the experimentally tested values of norethindrone serum level versus time, reported in table VIII, obtained by use of example 1 transdermal formulation.

Tables VII and VIII and graphics of FIG. 1 and 2 illustrates the result obtained.

TABLE VII

BIOAVAILABILITY STUDY RESULTS
Serum Levels of Estradiol (pg/ml)

| Time (h) | 0 | 2 | 6 | 12 | 24 | 30 | 36 | 48 | 54 | 60 | 72 |
|---|---|---|---|---|---|---|---|---|---|---|---|
| Moan | 6,37 | 32,78 | 20,54 | 26,81 | 27,61 | 39,30 | 30,34 | 35,89 | 65,21 | 48,69 | 43,74 |
| SEM | 1,13 | 6,42 | 1,75 | 6,17 | 2,96 | 5,84 | 3,26 | 3,84 | 6,19 | 5,08 | 4,75 |

TABLE VIII

Serum Levels of Norethindrone (pg/ml)

| Time (h) | 0 | 2 | 6 | 12 | 24 | 30 | 36 | 48 | 54 | 60 | 72 |
|---|---|---|---|---|---|---|---|---|---|---|---|
| Moan | 93 | 1407 | 1394 | 1908 | 2695 | 3461 | 3096 | 3713 | 5610 | 4904 | 4899 |
| SEM | 16 | 465 | 1332 | 252 | 299 | 427 | 445 | 390 | 362 | 592 | 345 |

I claim:

1. A gel for transdermal administration consisting essentially of:
   an active selected from the group consisting of an estrogen, a progestin, and mixtures thereof;
   a permeation enhancing effective amount of a monoalkyl ether of diethylene glycol and an aliphatic alcohol represented by $CH_3(CH_2)_nCH_2OH$, wherein n=8–16,
   a mixture of a $C_{2-4}$ alkanol, a glycol and water;
   a polymer or copolymer of acrylic acid; and
   a tertiary amine.

2. The gel according to claim 1 wherein the active is selected from the group consisting of 17-β-estradiol, norethindrone and mixtures thereof.

3. The gel according to claim 1 wherein the active is selected from the group consisting of 17-β-estradiol, norethindrone acetate and mixtures thereof.

4. The gel according to claim 1 wherein the aliphatic alcohol is lauryl alcohol, the monoalkyl ether of diethylene glycol is monomethyl- or monoethyl-ether, the $C_{2-4}$ alkanol is ethanol, the glycol is propylene glycol and the tertiary amine is triethanolamine.

5. The gel according to claim 1 containing between 0.02 and 0.09% (w/w) of 17-β-estradiol, between 0.30 and 1.50% (w/w) of norethindrone acetate, between 0.4 and 6.0% (w/w) of lauryl alcohol, between 1 and 15% (w/w) of diethylene glycol monoethyl ether, between 20 and 65% (w/w) of ethanol, between 1 and 12% (w/w) of propylene glycol, between 20 and 65% (w/w) of water, between 0.5 and 4% (w/w) of polymer or copolymer of acrylic acid, between 0.05 and 1% (w/w) of triethanolamine.

6. The gel according to claim 1 containing: 17-βestradiol 0.06% (w/w), norethindrone acetate 1.20% (w/w), lauryl alcohol 2.00% (w/w), diethylene glycol monoethyl ether 5.00% (w/w), ethanol 44.49% (w/w), propylene glycol 6.0% (w/w), water 39.45% (w/w), polymer or copolymer of acrylic acid 1.20% (w/w), triethanolamine 0.40% (w/w), flavouring agents 0.20% (w/w).

7. The gel according to claim 1 wherein the polymer or copolymer of acrylic acid is a carbomer.

8. The gel according to claim 1 wherein the active comprises 17-β-estradiol and norethindrone acetate in a weight ratio of 1:20.

9. The gel according to claim 1 wherein the aliphatic alcohol is n-decanol and is present in an amount of 1% (w/w) of the gel.

10. The gel according to claim 1 wherein the aliphatic alcohol is oleyl alcohol and is present in an amount of 1% (w/w) of the gel.

11. The gel according to claim 1 wherein the active comprises 17-β-estradiol and norethindrone in a weight ratio of 1:8.

12. The gel according to claim 1 wherein the active comprises 17-β-estradiol and medroxiprogesterone acetate in a weight ratio of 1:5.

13. The gel according to claim 1 wherein the progestin is selected from the group consisting of norethindrone acetate, norethindrone, norgestimate, medroxiprogesterone, progesterone, progesterone acetate, norgestrel, chlormadinone and gestadene.

14. The gel according to claim 1 wherein the active is a mixture of an estrogen and a progestin.

* * * * *

UNITED STATES PATENT AND TRADEMARK OFFICE
CERTIFICATE OF CORRECTION

PATENT NO. : 5,891,462
DATED : April 6, 1999
INVENTOR(S) : Dario CARRARA

It is certified that error appears in the above-identified patent and that said Letters Patent is hereby corrected as shown below:

ON THE TITLE PAGE:
item
[54] change the title from "COMPOSITION FOR TRANSDERMALADMINISTRATION OF AN ESTROGEN" to
COMPOSITION FOR TRANSDERMAL ADMINISTRATION OF AN ESTRGEN, A PROGESTIN OR A MIXTURE THEREOF--; and col. 1.
Title page, item
[73] after "Netherlands" add --Antilles--

Signed and Sealed this

Third Day of October, 2000

Attest:

Q. TODD DICKINSON

*Attesting Officer*     *Director of Patents and Trademarks*